United States Patent [19]

Hoare et al.

[11] Patent Number: 5,011,933
[45] Date of Patent: Apr. 30, 1991

[54] NITRATION OF PHENYL TRIAZOLINONES

[75] Inventors: John H. Hoare, Hamilton Square; Marc Halfon, Cranberry, both of N.J.

[73] Assignee: FMC Corporation, Philadelphia, Pa.

[21] Appl. No.: 485,106

[22] Filed: Feb. 26, 1990

[51] Int. Cl.$^5$ .......................................... C07D 249/12
[52] U.S. Cl. ................................................ 548/263.2
[58] Field of Search ..................................... 548/263.2

[56] References Cited

U.S. PATENT DOCUMENTS 4,818,275  4/1989  Theodoridis ........................... 71/92
4,845,232  7/1989  Matsui et al. ..................... 548/263.2

FOREIGN PATENT DOCUMENTS 62-277366 12/1987  Japan ............................... 548/263.2

OTHER PUBLICATIONS

R. B. Moodie et al., J. Chem. Soc. Perkin Trans. II (1985), pp. 1457–1464.
M. M. Melhuish, J. Chem. Soc. Perkin Tarns. II (1988), pp. 1637–1642.
Kirk, R. E.; Othmer, D. F., I, "Encyclopedia of Chemical Technology", 1st ed.; Interscience: New York, 1952; vol. 9, pp. 314–316.
Kirk—Othmer, II, "Encyclopedia of Chemical Technology", 3rd ed.; Wiley, New York, vol. 15, pp. 841–847.
Moodie et al., "Electrophilic Aromatic Substitution, etc.", CA 104:87882b (1986).
Melhuish et al., "Electrophilic Aromatic Substitution, etc.", CA 110:113980c (1989).

Primary Examiner—David B. Springer
Assistant Examiner—Patricia L. Morris
Attorney, Agent, or Firm—Robert M. Kennedy; Abner Sheffer

[57] ABSTRACT

Process for the nitration of a compound of formula I below with nitric acid in sulfuric acid, according to the following general equation:

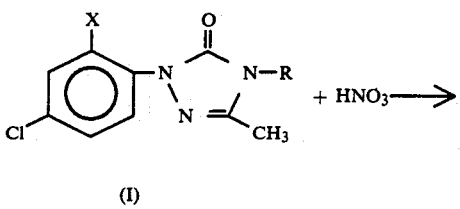

(I)

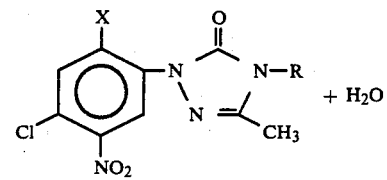

where X is a Cl or F and R is haloalkyl, for example $CHF_2$ or $CF_2CHF_2$, in which the improvement comprises carrying out said reaction in fuming sulfuric acid.

7 Claims, No Drawings

NITRATION OF PHENYL TRIAZOLINONES

This invention relates to the nitration of a compound of formula I below with nitric acid in sulfuric acid, according to the following general equation:

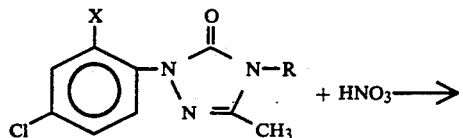

(I)

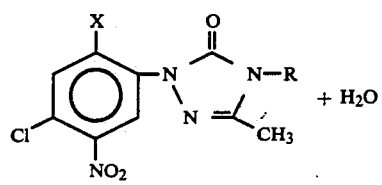

where X is Cl or F and R is haloalkyl, for example $CHF_2$ or $CF_2CHF_2$. The general process is illustrated, for instance, in U.S. Pat. No. 4,818,275, Examples 1G and 16A, in which the reaction is carried out with 70% nitric acid in concentrated sulfuric acid.

It has now been found that by carrying out the reaction in fuming sulfuric acid, higher yields are obtained and the by-product formation of the corresponding 6-nitro isomer can be prevented or substantially decreased. Preferably the $SO_3$ content of the fuming sulfuric acid is such that the number of moles of $SO_3$ is at least equal, or almost equal, to the total number of moles of water. The total number of moles of water is the sum of the initial number of moles of water (such as water introduced with the reactants, e.g. in the 70% nitric acid which may be used as a reactant) plus the number of moles of water which would be formed during the reaction shown above (i.e., one mole of water would be formed for each reacted mole of $HNO_3$). The $SO_3$ reacts with the water to form $H_2SO_4$, and it is preferred that the number of moles of $SO_3$ in relation to the total number of moles of water be such that the final water concentration in the sulfuric acid is at most 4% by weight (i.e. an $H_2O:H_2SO_4$ weight ratio of at most 4:96), more preferably zero. More preferably the relative amounts of $SO_3$ and total water are such that the concentration of $SO_3$ remaining in the sulfuric acid at the end of the reaction is at least about 5% by weight (i.e. an $SO_3:H_2SO_4$ weight ratio of at least about 5:95), and still more preferably at least about 10% by weight (i.e. an $SO_3:H_2SO_4$ weight ratio of at least about 10:90). The total amount of water may be calculated from the known concentration of water in the reactants and the fact that one mole of water would be formed for each nitro substituent formed on the aromatic reactant.

The following Examples illustrate this invention further. In these examples all proportions are by weight, and temperatures are degrees C. unless otherwise indicated.

EXAMPLE 1

5.67g of 98% nitric acid (88.2 millimoles $HNO_3$ and 6.3 millimoles water) was added at room temperature to a dispersion of 16.8g (57.1 millimoles) of 4,5-dihydro-3-methyl-4-difluoromethyl-1-(2, 4-dichlorophenyl)-1,2,4-triazol-5(1H)-one in 145.5g of 15% oleum (273 millimoles $SO_3$), and the mixture was allowed to react, with stirring, to approximately 100% conversion as shown by the disappearance of the organic reactant (about 2.5 hours). At the start of the reaction some of the organic reactant was in an undissolved, dispersed state, bu it all went into solution during the reaction. At the conclusion of the reaction, the calculated amount of water in the mixture was zero, and the calculated weight of $SO_3$ was about 11% by weight (i.e. an $SO_3:H_2SO_4$ weight ratio of about 11:89). The yield of 4,5-dihydro-3-methyl-4-difluoromethyl-1-(2, 4-dichloro-5-nitrophenyl)-1,2,4-triazol-5(1H)-one was about 97%. The ratio of the isomers having the nitro group at the 5, 3 and 6-positions, respectively, was about 98:2:0.

COMPARATIVE EXAMPLE

The procedure of Example 1 was repeated except that the reaction mixture contained additional water (and additional $H_2SO_4$) so that the calculated final water concentration in the sulfuric acid at the end of the reaction was about 6% (i.e. an $H_2O:H_2SO_4$ weight ratio of 6:94). The yield of 4,5-dihydro-3-methyl-4-difluoromethyl-1-(2, 4-dichloro-5-nitrophenyl)-1,2,4-triazol-5(1H)-one was about 76% and the ratio of the isomers having the nitro group at the 5, 3 and 6-positions, respectively, was about 90:5:5.

In Example 1 above the weight ratio of the organic reactant to $H_2SO_4$ is about 12:88; other ratios may be used, e.g. ratios in the range of about 1:99 to 25:75, preferably about 5:95 to 15:85.

In Example 1 the mole ratio of $HNO_3$ to organic reactant is about 1½:1; other ratios may be used, e.g. ratios in the range of about 1:1 to 5:1, preferably about 1.1:1 to 1.7:1.

In Example 1 the reaction is carried out at about room temperature, maintained by an ice bath; other temperatures may be used, e.g. temperatures in the range of about 0° to 100° C., preferably about 10° to 70° C., such as about 20° to 40° C. The pressure in Example 1 is atmospheric; however, superatmospheric or subatmospheric pressure may be used.

In Example 1, 15% oleum is used. Oleum of lower or higher concentration may be employed instead. Also, the fuming sulfuric acid may be formed in situ in a reaction mixture made with concentrated sulfuric acid, as by adding $SO_3$ to such a mixture during the course of the reaction.

It is understood that the foregoing detailed description is given merely by way of illustration and that variations may be made therein without departing from the spirit of the invention.

What is claimed is:

1. Process for the nitration of a compound of formula I below with nitric acid in sulfuric acid, according to the following general equation:

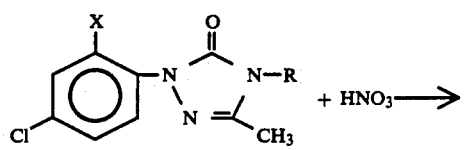

(I)

-continued

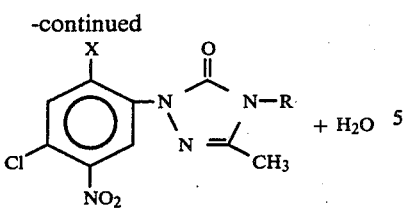 + $H_2O$ where X is a Cl or F and R is haloalkyl, in which the improvement comprises carrying out said reaction in fuming sulfuric acid.

2. Process as in claim 1 in which R is $CHF_2$ or $CF_2CHF_2$.

3. Process as in claim 2 in which the $SO_3$ content of the fuming sulfuric acid in relation to the total number of moles of water is such that the $H_2O:H_2SO_4$ weight ratio is at most 4:96 at the end of the reaction.

4. Process as is in claim 2 in which the $SO_3$ content of the fuming sulfuric acid in relation to the total number of moles of water is such at that the water concentration at the end of the reaction is about zero.

5. Process as in claim 4 in which the $SO_3$ content fuming sulfuric acid in relation to the total number of moles of water is such that the $SO_3:H_2SO_4$ ratio at the end of the reaction is at least about 5:95.

6. Process as in claim 4 in which the $SO_3$ content of the fuming sulfuric acid in relation to the total number of moles of water is such that the $SO_3:H_2SO_4$ ratio at the end of the reaction is at least about 10:90.

7. Process as in claim 2 in which the weight ratio of said compound of formula I to $H_2SO_4$ is in the range of about 1:99 to 25:75, the mole ratio of $HNO_3$ to the said compound is in the range of about 1:1 to 5:1 and the reaction temperature is in the range of about 0° to 100° C.

* * * * *